United States Patent
Jung

(10) Patent No.: US 10,253,348 B2
(45) Date of Patent: Apr. 9, 2019

(54) MICROSTRUCTURE FOR CAPTURING AND RELEASING MICROORGANISM

(71) Applicant: QUANTA MATRIX CO,. LTD., Seoul (KR)

(72) Inventor: Yong Gyun Jung, Seoul (KR)

(73) Assignee: QUANTAMATRIX INC., Seoul (KR)

( * ) Notice: Subject to any disclaimer, the term of this patent is extended or adjusted under 35 U.S.C. 154(b) by 253 days.

(21) Appl. No.: 14/413,008

(22) PCT Filed: Jul. 4, 2013

(86) PCT No.: PCT/KR2013/005947
§ 371 (c)(1),
(2) Date: Mar. 19, 2015

(87) PCT Pub. No.: WO2014/007560
PCT Pub. Date: Jan. 9, 2014

(65) Prior Publication Data
US 2015/0361477 A1    Dec. 17, 2015

(30) Foreign Application Priority Data

Jul. 6, 2012 (KR) .................. 10-2012-0073974

(51) Int. Cl.

| C12M 1/12 | (2006.01) |
|---|---|
| C12M 1/30 | (2006.01) |
| C12Q 1/24 | (2006.01) |
| C12N 11/02 | (2006.01) |
| C12N 11/06 | (2006.01) |
| C12N 11/08 | (2006.01) |
| C12N 11/14 | (2006.01) |

(52) U.S. Cl.
CPC .............. *C12Q 1/24* (2013.01); *C12M 25/00* (2013.01); *C12M 33/02* (2013.01); *C12N 11/02* (2013.01); *C12N 11/06* (2013.01); *C12N 11/08* (2013.01); *C12N 11/14* (2013.01)

(58) Field of Classification Search
None
See application file for complete search history.

(56) References Cited

U.S. PATENT DOCUMENTS

| 5,112,952 | A | 5/1992 | Mallia et al. |
|---|---|---|---|
| 9,593,160 | B2 * | 3/2017 | Ingber .............. C07K 16/12 |

FOREIGN PATENT DOCUMENTS

| CN | 101675164 A | 3/2010 |
|---|---|---|
| CN | 102302877 A | 1/2012 |
| CN | 102500291 | 6/2012 |
| JP | 2006-094822 A | 4/2006 |
| KR | 10-1995-0008383 A | 4/1995 |
| WO | WO2013012924 | * 1/2013 |
| WO | 2013116513 | 8/2013 |

OTHER PUBLICATIONS

International Search Report for PCT/KR2013/005947 dated Nov. 1, 2013 from Korean Intellectual Property Office.
Van Emmerik, L. C. et al., Binding of marinan-binding protein to various bacterial pathogens of meningitis, Clin Exp Immunol 1994; 97; 411-416.
Sepharose 2B 60-200 micrometer bead diameter; Sigma-Aldrich, Feb. 19, 2016.
Neth, Olaf et al., Mannose-Binding Lectin Binds to a Range of Clinically Relevant Microorganisms and Promotes Complement Deposition, Infection and Immunity, Feb. 2000, p. 688-693, vol. 68, No. 2, American Society for Microbiology.

* cited by examiner

*Primary Examiner* — Blaine Lankford
(74) *Attorney, Agent, or Firm* — STIP Law Group, LLC

(57) ABSTRACT

Provided is a method for capture and release of microorganisms using microstructures. The method includes providing microstructures coated with a protein for attachment/detachment of microorganisms, mixing the microstructures with a solution containing substances assisting in attachment of microorganisms in a solution containing microorganisms to prepare a mixed solution, stirring the mixed solution to attach the microorganisms to the microstructures, separating the microorganism-attached microstructures from the mixed solution; and exposing the microstructures to an environment where the substances assisting in attachment of the microorganisms are present at a low concentration to detach the microorganisms from the microstructures.

13 Claims, 8 Drawing Sheets

[Fig. 1]
(a)
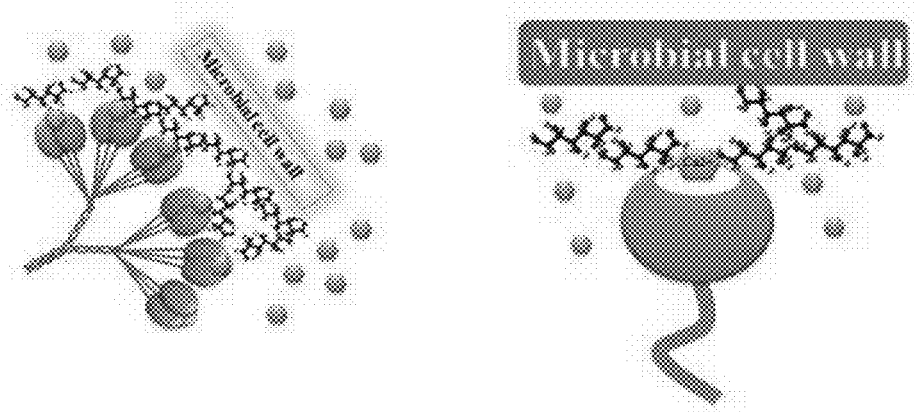
(b)
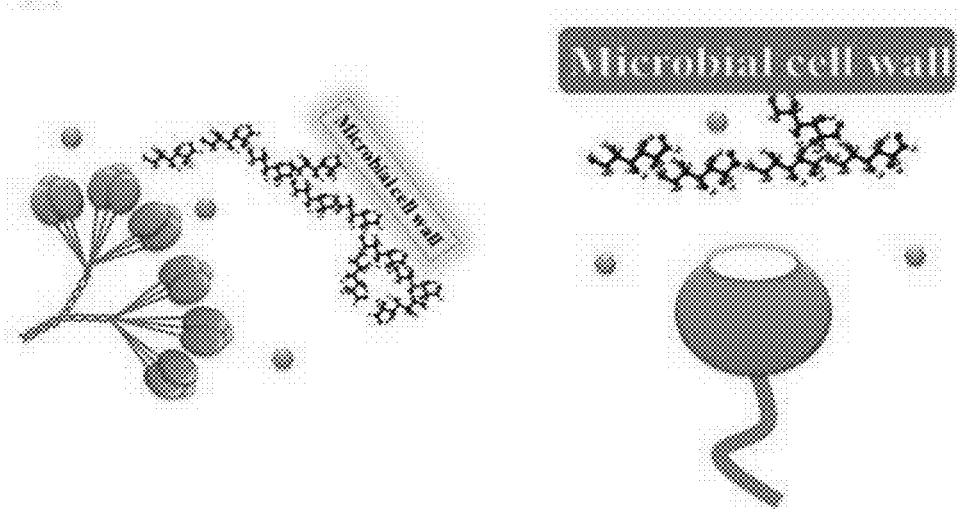
 Ca²⁺   MBL mutimer   Individual CRD

[Fig. 2]
(a)
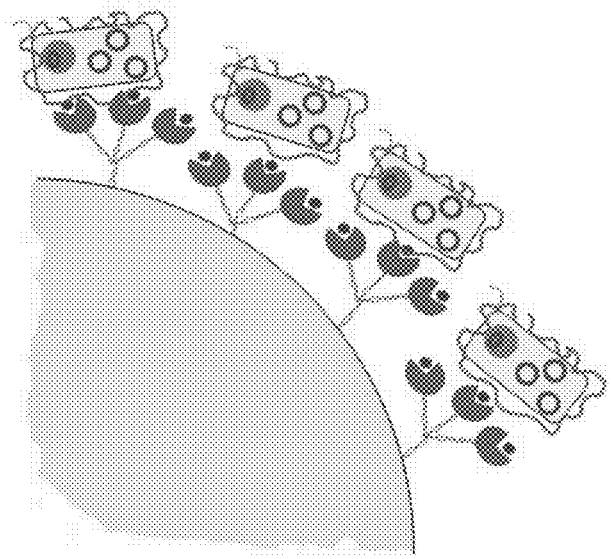
○ : Microstructure   : MBL   : Bacteria
(b)
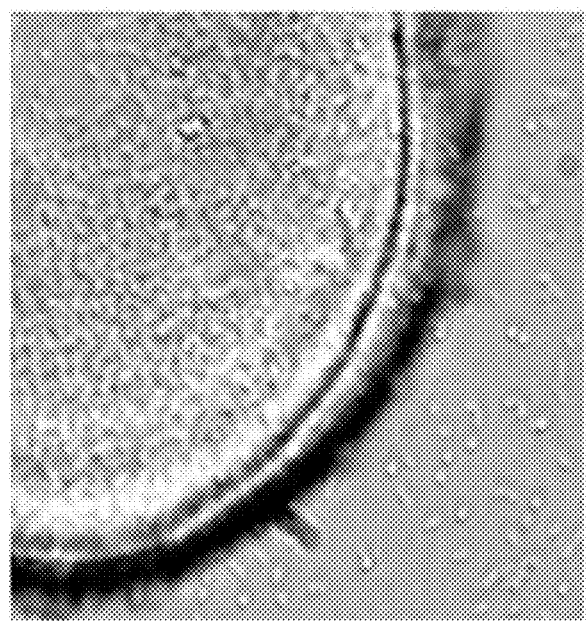

[Fig. 3]

```
                    ┌─────────┐
                    │  Start  │
                    └─────────┘
                         │
                         ▼
    ┌─────────────────────────────────────────────┐
    │ Provide microstructures coated with protein │──S1
    │ for attachment/detachment of microorganisms │
    └─────────────────────────────────────────────┘
                         │
                         ▼
    ┌──────────────────────────────────────────────────┐
    │ Mix solution containing microorganisms, the      │
    │ microstructures, and solution containing         │──S2
    │ substances assisting in attachment of            │
    │ microorganisms to prepare mixed solution         │
    └──────────────────────────────────────────────────┘
                         │
                         ▼
    ┌─────────────────────────────────────────────┐
    │ Stir the mixed solution to attach the       │──S3
    │ microorganisms to the microstructures       │
    └─────────────────────────────────────────────┘
                         │
                         ▼
    ┌─────────────────────────────────────────────┐
    │ Separate the microorganism-attached         │──S4
    │ microstructures from the mixed solution     │
    └─────────────────────────────────────────────┘
                         │
                         ▼
    ┌──────────────────────────────────────────────────────┐
    │ Expose the microstructures to environment where the  │
    │ substances assisting in attachment of the            │──S5
    │ microorganisms are present at low concentration to   │
    │ detach the microorganisms from the microstructures   │
    └──────────────────────────────────────────────────────┘
                         │
                         ▼
                    ┌─────────┐
                    │   End   │
                    └─────────┘
```

[Fig. 4]
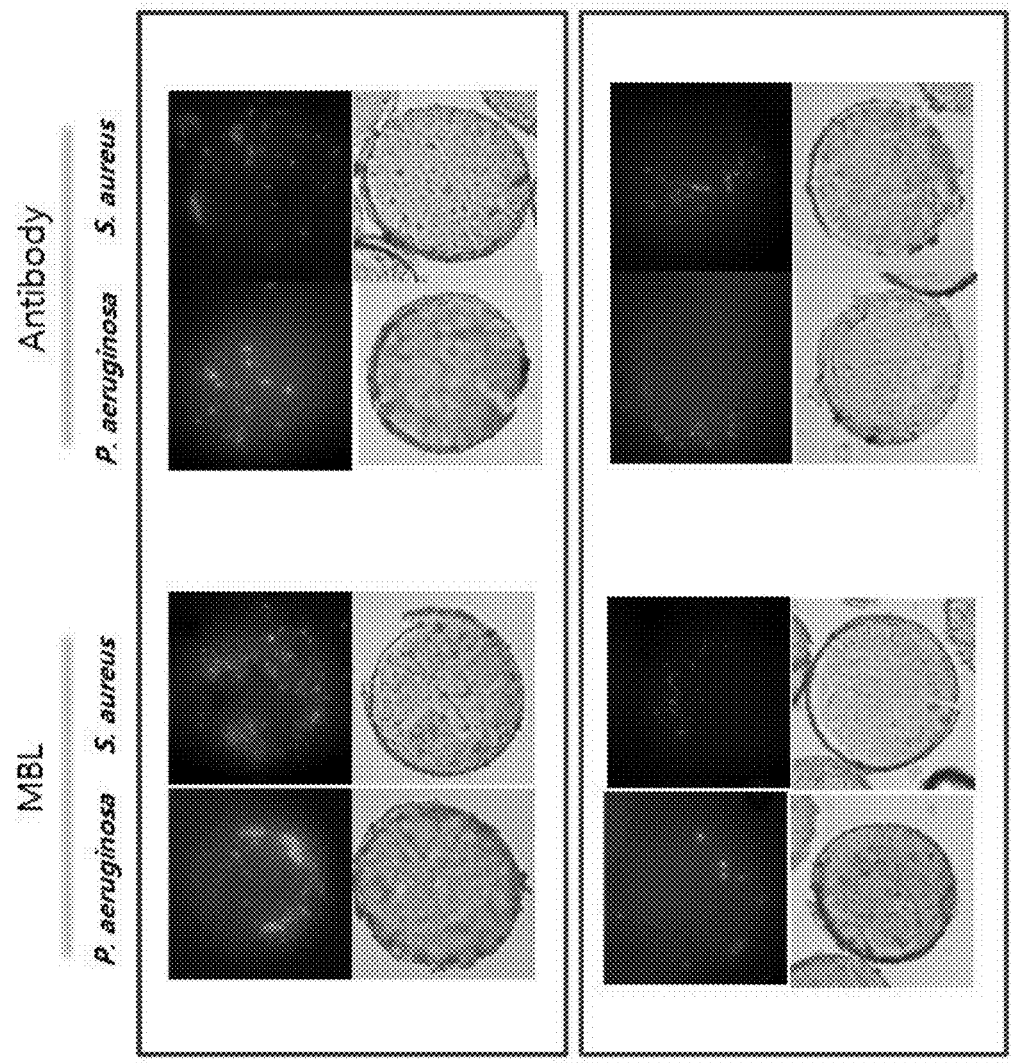
Comparison of the ability of antibody-microstructures to attach microorganisms with that of MBL-microstructures
Comparison of the ability of antibody-microstructures to detach microorganisms with that of MBL-microstructures

[Fig. 5]
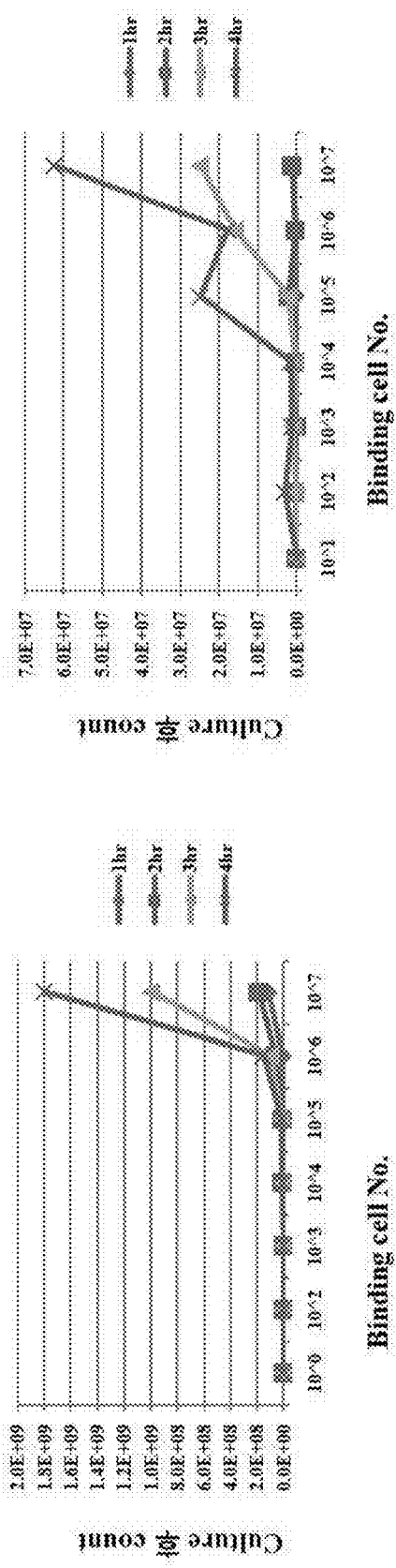
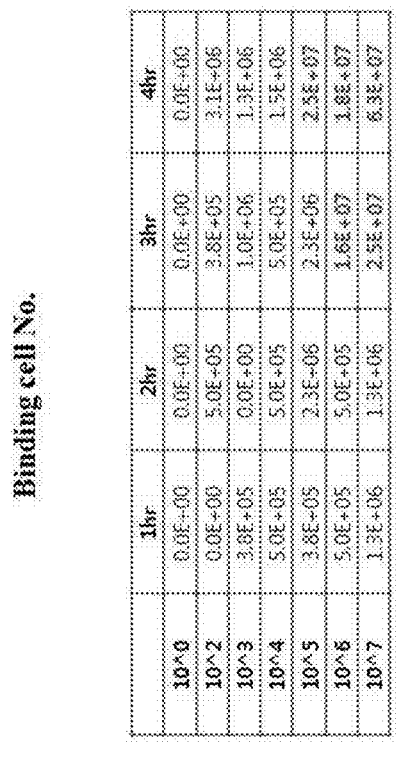

[Fig. 6]
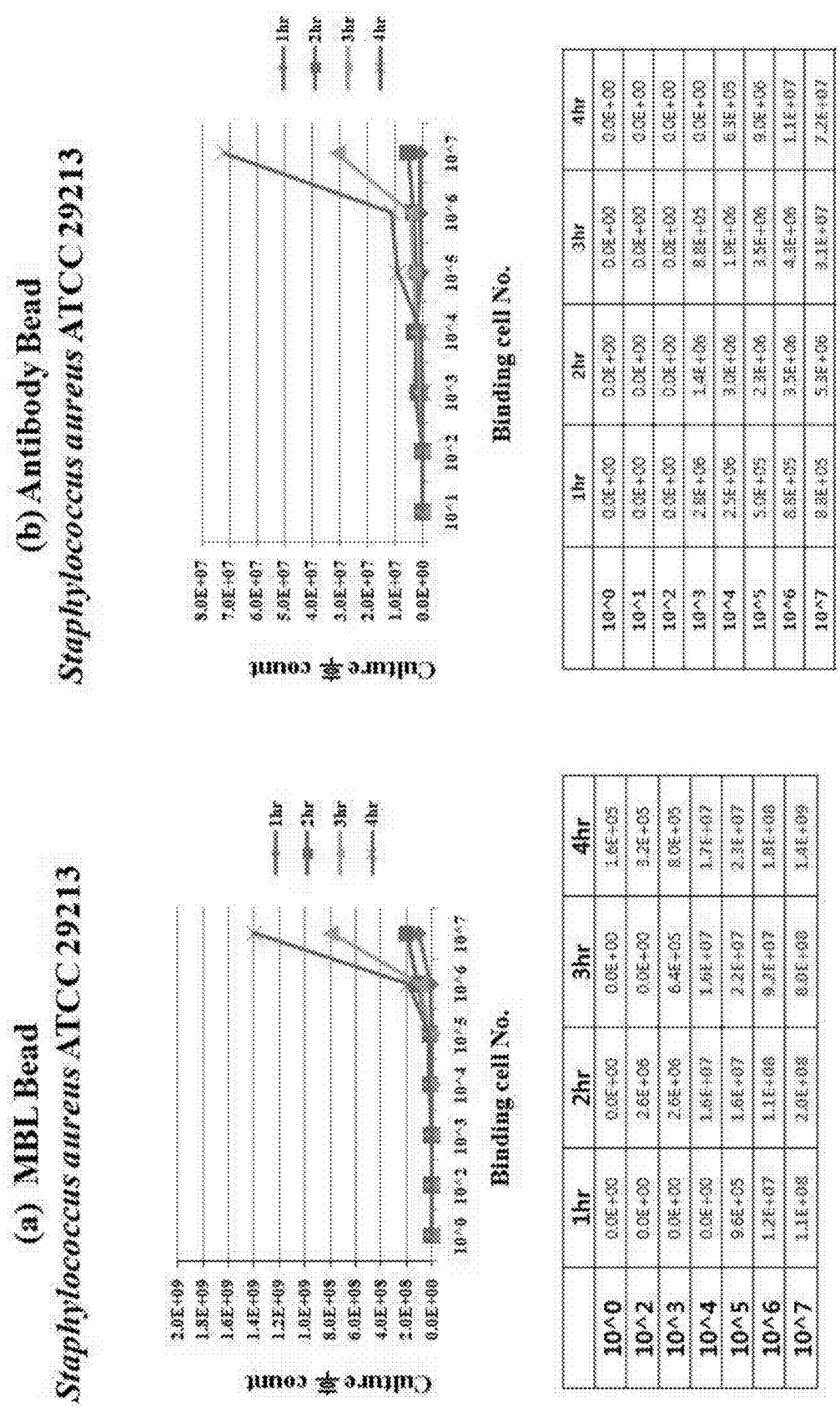

[Fig. 7]
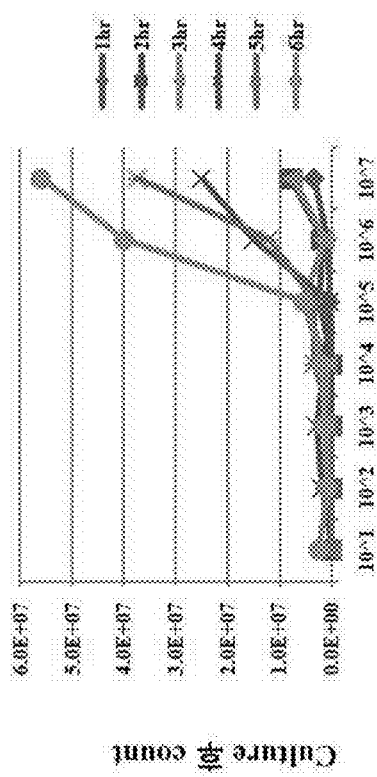
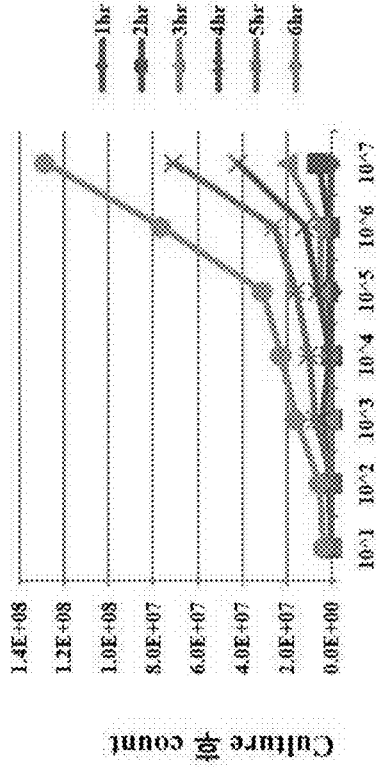

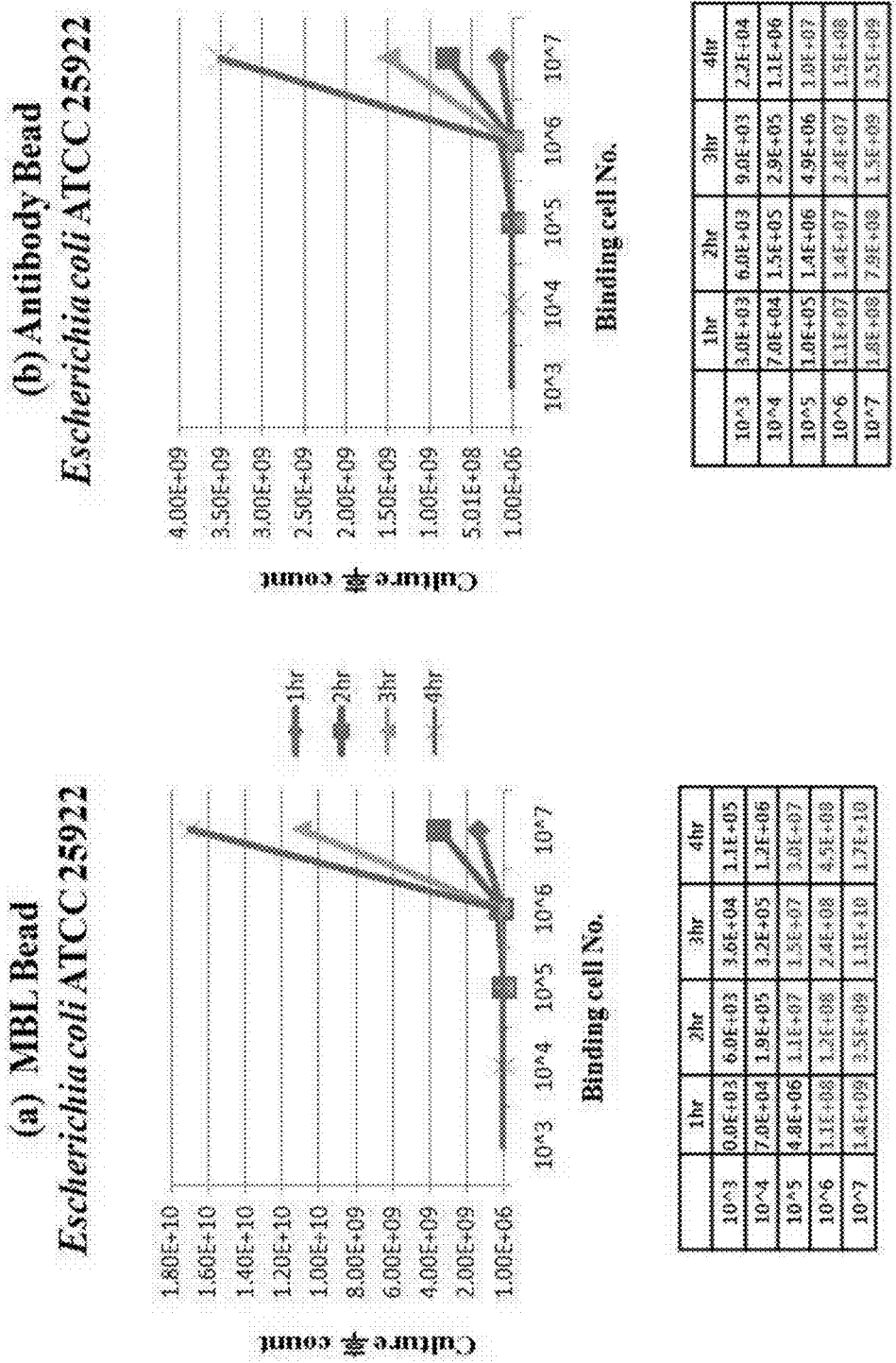

MICROSTRUCTURE FOR CAPTURING AND RELEASING MICROORGANISM

CROSS REFERENCE TO PRIOR APPLICATIONS

This application is a National Stage Application of PCT International Patent Application No. PCT/KR2013/005947 filed on Jul. 4, 2013, under 35 U.S.C. § 371, which claims priority to Korean Patent Application No. 10-2012-0073974 filed on Jul. 6, 2012, which are all hereby incorporated by reference in their entirety.

TECHNICAL FIELD

The present disclosure relates to a microstructure for capture and release of microorganisms.

BACKGROUND ART

For effective treatment of a septicemia or bacteremia suspected patient, blood culture testing is performed to accurately diagnose what causative organism is responsible for septicemia and what therapeutic agent is effective against the causative organism. Generally, the blood culture testing is performed by the following procedure. First, blood is aseptically collected from the patient. For the blood collection, a suitable tool such as a syringe is used to keep the skin from being contaminated by microbes normally present on the skin and microbes present in ambient environments. The blood samples are mixed with liquid blood culture media and observed whether microorganisms grow during culture at 37° C., typically for 1-2 days. The media inoculated with the blood are separately cultured under aerobic and anaerobic conditions. As a result, anaerobic microbes (incapable of growing in the presence of oxygen) as well as aerobic microbes (capable of growing in the presence of oxygen) or facultative anaerobic microbes (capable of growing with or without oxygen) can be cultured in the media. The bottoms of culture bottles containing the media are usually coated with chemicals that tend to discolor or emit fluorescence when microorganisms grow. Thus, the use of blood culture systems capable of recognizing color changes or fluorescence enables automatic detection of the growth of microorganisms in the media. After the microorganisms are extracted from the patient and cultured until the number of the microorganisms reaches an optimum level ($10^5$ cell/ml), subsequent processes (such as identification of the pathogenic strain and antibiotic susceptibility testing) are performed. At this time, pure culture is required for selectively isolating the pathogenic strain from the blood culture solutions and culturing the pathogenic strain. According to a general pure culture method, the culture solutions (containing the microorganisms) after blood culture are plated on agar media to obtain a necessary amount of the microbe. At this time, it takes about 16 to 24 hours for the microbe to form colonies. The conventional pure culture method requires a relatively long time, which remarkably deteriorates the therapeutic effect on bacterial septicemia. Therefore, a shorter culture time is required for more rapid antibiotic susceptibility testing.

The conventional method also requires a process for isolating microorganisms from foods or natural environments to identify and culture the microorganisms. However, microorganisms present in very small quantities in such environments are not easy to isolate. Even when microorganisms are present in relatively large quantities, a time-consuming process for culturing the microorganisms is necessary to isolate the microorganisms.

Therefore, there is a need for a method of isolating microorganisms from various environments, for example, tissues, blood, feces, and urine derived from organisms, foods, and natural environments, in an effective and time-consuming manner.

DETAILED DESCRIPTION OF THE INVENTION

According to one aspect of the present disclosure, structures for capture and release of microorganisms are provided which include microstructures, each of which has a surface area where one or more microorganisms are attachable, and a protein coated on the microstructures and capable of attachment/detachment of the microorganisms by artificial control.

According to another aspect of the present disclosure, a method for capture and release of microorganisms using microstructures is provided which includes providing microstructures coated with a protein for attachment/detachment of microorganisms, mixing the microstructures with a solution containing substances assisting in attachment of microorganisms in a solution containing microorganisms to prepare a mixed solution, stirring the mixed solution to attach the microorganisms to the microstructures, separating the microorganism-attached microstructures from the mixed solution, and lowering the concentration of the substances assisting in microorganism attachment to detach the microorganisms from the microstructures.

BRIEF DESCRIPTION OF THE DRAWINGS

FIG. 1 is a diagram showing a model in which bacteria are bound to or unbound from a human mannose-binding lectin (MBL).

FIG. 2 shows (a) a schematic diagram and (b) an actual optical microscope image illustrating a state in which bacteria are attached to an MBL-coated microstructure.

FIG. 3 is a flowchart illustrating one embodiment of a method for capture and isolation of microorganisms.

FIG. 4 shows optical microscope images showing the results of experiments comparing the bacteria capture and release properties of antibody-coated microstructures and MBL-coated microstructures.

FIGS. 5 to 8 show the number of cells recorded every hour after bacteria attached to MBL-coated microstructures and antibody-coated microstructures were isolated from the microstructures, followed by culture.

MODE FOR CARRYING OUT THE INVENTION

Embodiments of the present disclosure will now be described in detail with reference to the accompanying drawings. These embodiments are provided so that this disclosure is thorough, and will fully convey the scope of the disclosure to those skilled in the art. Accordingly, the present disclosure may be embodied in many different forms and should not be construed as limited to the exemplary embodiments set forth herein. In the drawings, the dimensions, such as widths, lengths and thicknesses, of elements may be exaggerated for clarity. The same reference numerals denote the same elements throughout the drawings. The drawings are explained from an observer's point of view. It will be understood that when an element is referred to as being "on"

another element, it can be directly on the other element, or one or more intervening elements may also be present there between.

In one aspect, the present disclosure provides novel structures for capture or release of microorganisms in an easy manner. The structures of the present disclosure include microstructures, each of which has a surface area where one or more microorganisms are attachable, and a protein coated on the microstructures and capable of attachment/detachment of the microorganisms by artificial control.

The microstructures are designed to be structurally suitable for capture and release of microorganisms. The surface area of each microstructure is large enough to capture one or more microorganisms. That is, the dimensions of each microstructure are larger than those of the microorganisms.

The term "microstructure" herein used refers to a structure whose dimensions are equal to or greater than those of the microorganisms such as bacteria and whose longest side is at least 1 µm. For example, each of the microstructures may be a structure that has at least one of its width, thickness, and length in the range of 1 µm to 1 mm. At least one of the width, thickness, and length dimensions of the microstructure may be typically from tens to hundreds of micrometers. The microstructure may have an isotropic structure such as a spherical, polyhedral, planar or rod-like structure. Alternatively, the microstructure may have an anisotropic structure or may be unshaped. For example, the microstructure may be a spherical structure having a diameter of tens of micrometers. Preferably, the microstructure is a planar or disc-shaped structure having a width of tens of micrometers. When the microstructures are planar in shape, at least one microorganism can be attached to each microstructure. In addition, a plurality of microorganisms are attached to and distributed on the front and rear sides of the planar microstructures. This planar distribution is advantageous in focusing on an object or determining the number of the microorganisms in a subsequent process for observing the microorganisms with an imaging system.

The microstructures may be manufactured by various techniques. For example, the continuous flow lithography disclosed in U.S. Patent Publication No. 2007/0105972 or the optofluidic lithography using a digital micromirror device (DMD) disclosed in Korean Patent No. 0875900 may be used to manufacture microstructures with various shapes, sizes, and chemical compositions in a faster and easier manner.

The microstructures may be polymers produced by curing a curable material such as a UV-curable polymer or monomer. The curable material may include a liquid-phase hydrophilic polymer capable of forming a hydrogel.

Examples of such curable materials capable of forming a hydrogel include silicon-containing polymers such as polydimethylsiloxane, polyacrylamide, polyethylene oxide, polyethylene glycol diacrylate, polypropylene glycol diacrylate, polyvinylpyrrolidone, polyvinyl alcohol, polyacrylate, and copolymers thereof. For example, since polyethylene glycol diacrylate (PEG-DA) as the curable material has acrylate functional groups at both ends of the polyethylene glycol (PEG) chain, it may be crosslinked to form a three-dimensional hydrogel via free radical polymerization. The curable material may further include any type of medium whose state can be changed from a liquid to a solid.

Irradiation of the curable material with UV light through a photomask pattern or a mask pattern formed in a digital micromirror device enables the manufacture of microstructures in various forms.

The microstructures are coated with the protein capable of attachment/detachment of the microorganisms by artificial control. The protein makes the microstructures suitable for capture and release of the microorganisms. The surface of the protein interacts with the microorganisms. The surface characteristics of the protein may be varied by artificially controlling such factors as pH, temperature, and external metal ion concentration. For example, the microstructures may capture or release the microorganisms in a predetermined pH range, a predetermined temperature range or a predetermined ion concentration range.

Each microstructure may further include a protective layer having functional groups. Preferably, a silica-coated layer is used as the protective layer. The introduction of functional groups such as carboxyl groups facilitates the coating of the protein for attachment/detachment of the microorganisms such as MBL.

When the microstructures are based on a hydrogel, the silica-coated layer increases the stability of the microstructures and prevents MBL from being absorbed into the hydrogel. Functional groups for the introduction of MBL may be introduced through the surface —OH groups of the silica-coated layer.

The protein may be bound to glycoproteins or carbohydrates present on the surfaces of the microorganisms. The microorganisms may be, for example, viruses, bacteria, and protozoa. The protein for attachment/detachment of the microorganisms may be, for example, a calcium-dependent serum protein. Specifically, the calcium-dependent serum protein may be a mannose-binding lectin (MBL). The mannose-binding lectin (MBL) is also called a mannose-binding protein (MBP). MBL is a calcium ion ($Ca^{2+}$)-dependent lectin (C-type lectin) that activates lectin pathway or functions as an opsonin to markedly improve the phagocytosis of leukocytes. The characteristics of the protein for attachment/detachment of the microorganisms can be artificially controlled by the substances assisting in microorganism attachment. For example, the MBL may be bound to the microorganisms by calcium ions.

FIG. 1 is a diagram showing a model in which bacteria as the microorganisms are bound to or unbound from a human mannose-binding lectin (MBL) as the protein. When calcium ions ($Ca^{2+}$) are present at a high concentration, the MBL is bound to sugar residues of the microbial cell walls via the calcium ions to hold the microbes with a strong force (see (a) of FIG. 1). Meanwhile, when calcium ions ($Ca^{2+}$) are present at a low concentration, the MBL is not bound to the microbial cell walls any longer, and as a result, the microbes are released (see (b) of FIG. 1).

Referring to FIG. 1, the MBL has 2 to 6 carbohydrate recognition domains (CRDs). MBL can seize sugars present on the surfaces of the microorganisms such as bacteria via the calcium ions. As a result, the MBL-coated microstructures can capture the microorganisms in an environment where the calcium ions are present at a high concentration (e.g., 20 mM or higher). MBL can advantageously capture almost all kinds of bacteria with high efficiency. Bacteria can be easily isolated from MBL by lowering the concentration of ambient calcium ions. The collected bacteria may be cultured or directly used for antibiotic susceptibility testing (AST).

FIG. 2 shows (a) a schematic diagram and (b) an actual optical microscope image illustrating a state in which the bacteria are attached to the MBL-coated microstructure. (b) of FIG. 2 shows a state in which *Bacillus subtilis* ATCC 6633 as the bacterial species is attached to a disc-shaped PEG as the microstructure. The microstructure has a diameter of 100 μm and a height of 25 μm.

In another aspect, the present disclosure provides a method for capture and isolation of microorganisms using microstructures. FIG. 3 is a flowchart illustrating one embodiment of the method for capture and isolation of microorganisms. Referring to FIG. 3, in step S1, microstructures coated with a protein for attachment/detachment of microorganisms are provided.

In step S2, the microstructures are mixed with a solution containing substances assisting in attachment of microorganisms in a solution containing microorganisms to prepare a mixed solution. The microorganisms may be, for example, bacteria present in general culture solutions, cultured bacteria after blood culture, or bacteria present in various environments, for example, blood, feces, urine or tissues derived from organisms, foods or natural environments. In the case where the microstructures are coated with MBL, the solution containing substances assisting in attachment of microorganisms may be, for example, a buffer solution for cells, such as TE or phosphate buffered saline containing calcium ions.

In step S3, the mixed solution is stirred to attach the microorganisms to the microstructures. For example, the mixed solution may be appropriately stirred by shaking at 50 to 100 rpm at 30 to 37° C.

In step S4, the microorganism-attached microstructures are separated from the mixed solution. Filtration may be used to separate the microstructures. Alternatively, magnetic separation may be used when the microstructures include a magnetic material.

In step S5, the microstructures are exposed to an environment where the substances assisting in attachment of the microorganisms are present at a low concentration. Due to this exposure, the microorganisms can be detached from the microstructures. The microorganism-attached microstructures may be exposed to a solution where the substances assisting in attachment of the microorganisms are excluded, and as a result, the microorganisms can be isolated from the microstructures. For example, the solution containing the MBL-microstructures attached to the microorganisms due to the presence of calcium ions may be treated with TE or PBS free of calcium ions to remove calcium ions therefrom, and the microstructures are then placed in an ordinary microorganism medium. Since the MBL is bound to the surfaces of the microorganisms via calcium ions, the exposure of the microorganism-attached microstructures to the liquid environment where the calcium ions are present at a low concentration (e.g., 1 mM or less) enables isolation of the calcium ions from the MBL, facilitating detachment of the microorganisms from the microstructures. The detached microorganisms remain substantially intact and can thus be efficiently cultured in a medium in a subsequent step.

As described above, the use of the MBL-coated microstructures enables the capture of unknown kinds of bacteria present at low concentrations. Thereafter, the captured bacteria can be easily isolated from the microstructures in a medium, resulting in an increase in the culture efficiency of the bacteria. Therefore, the method of the present disclosure can be used in the following applications.

First, the present disclosure can be applied to a bacteria antibiotic susceptibility testing system. The high capture rate and culture efficiency of the method according to the present disclosure can significantly shorten the time required for pure culture (normally 16-24 hours). For example, according to the present disclosure, blood containing bacteria at a concentration of $10^5$ cfu/ml can be cultured to a higher concentration of $10^7$ cfu/ml within about 3 hours.

Second, the present disclosure can be used to effectively isolate microorganisms (e.g., bacteria or viruses) present in various environments, for example, tissues, blood, feces or urine derived from organisms, foods or natural environments. As a result, the time required to identify the microorganisms can be reduced. If needed, the present disclosure can also be used to effectively culture the microorganisms.

Third, the present disclosure can be used for bacteria storage. CRYOBANK™, a commercial system for storage and preservation of bacterial strains, uses ceramic beads whose ability to adsorb bacteria is poor, making it difficult to store a number of the bacteria therein. Accordingly, the present disclosure is expected to be more advantageous in terms of bacteria capture and culture efficiency compared to the conventional bead system.

Fourth, the present disclosure can also be used in applications where bacteria are captured and the captured bacterial cells are subjected to lysis using beads to efficiently isolate DNA and proteins, like a bacteria capture kit from Hyglos. Since the conventional commercial bead lysis kit uses antibodies to capture bacteria, it can be applied to particular strains and cannot be applied to a wide range of strains. In contrast, the present disclosure can be used to easily capture various kinds of strains.

The advantages of the present disclosure are distinguished from the prior art. According to the prior art, methods for bacteria collection are broadly divided into two groups. One is associated with the attachment of bacterial antibodies to beads (Sanchez, J. 8t Jonson, G. Binding of bacteria to carbohydrates immobilized on beads to demonstrate the presence of cell-associated hemagglutinins in Vibrio cholerae. APMIS 98: 353-357, 1990), and the other is associated with the coating of MBL on nanobeads (Keun-Hwa Park, Kenji Kurokawa, Human Serum Mannose-binding Lectin Senses Wall Teichoic Acid Glycopolymer of *Staphylococcus aureus*, Which is Restricted in Infancy VOLUME 285/NUMBER 35/Aug. 27, 2010). In the former method, one kind of bacteria is highly specifically bound to a particular kind of antibody. However, the use of antibodies does not ensure the capture of various bacteria or unknown bacteria with high efficiency. According to the latter method, nanometer-scale beads are attached to micrometer-scale bacteria to capture the bacteria. This method ensures capture of the bacteria with high efficiency but has difficulty in detaching the beads from the bacteria. Further, the nanometer-sized beads may be toxic to the cells, affecting the growth of the bacteria. As a consequence, this method is difficult to apply to the culture of the captured bacteria or use in other applications such as AST. That is, the use of nanobeads is helpful in determining the presence of bacteria but makes the method difficult to use for purposes other than collection and identification of bacteria.

The present disclosure will be explained in more detail with reference to the following examples. However, these examples are not intended to limit the spirit of the present disclosure.

EXAMPLES

Manufacture of Microstructures

PEG-DA was cured by optofluidic maskless lithography (OFML) to produce disc-shaped beads with various diameters of 50-200 μm and thicknesses of about 10-50 μm, mainly a 100 μm diameter and a 25 μm thickness. The disc-shaped beads were allowed to contain a magnetic material in such an amount that the volume ratio of the PEG-DA to the magnetic material was 10:1. Due to the presence of the magnetic material, the beads were easily separated from a mixed solution in the subsequent process. Silica was coated on the bead surfaces. Thereafter, antibodies or MBL was attached to the bead surfaces using a catalyst such as ECD/NHS. The antibodies or MBL was added in such an amount that the concentration reached about 1-125 µg/ml (typically 5 µg/ml).

Comparison of Bacteria Capture and Release Properties of the MBL-Coated Microstructures and the Antibody-Coated Microstructures The bacteria capture and release properties of the MBL-coated microstructures were compared with those of the antibody-coated microstructures in accordance with the following experimental procedure.

First, blood infected with bacteria was cultured until the number of cells reached a maximum of $10^8$/ml. Samples having concentrations of $10^0$-$10^7$ count/ml were prepared. The microstructures were coated with antibodies specific to gram-negative bacteria and gram-positive bacteria. Separately, the microstructures were coated with MBL. The microstructures were shaken at 50-100 rpm in the bacteria culture solutions (each 1 ml) at 37° C. for 1 hr. The number of the microstructures in each bacteria culture solution was adjusted to 5000 counts. As a result of the shaking, the bacteria were attached to the microstructures.

After completion of the culture, a magnetic or filtration method was used to isolate the bacteria-attached beads. Thereafter, the beads were transferred to fresh culture solutions. The bacteria were allowed to be naturally detached from the structures. The pure bacteria isolated from the microstructures were cultured over 1-4 hours. The numbers of the cultured bacteria released from the antibody-coated microstructures and the MBL-coated structures were measured and compared every hour (C-chip, NanoEntek).

FIG. 4 shows optical microscope images showing the results of experiments comparing the bacteria capture and release properties of the antibody-coated microstructures and the MBL-coated microstructures. In the top images of FIG. 4, the ability of the MBL-microstructures (left) to attach the microorganisms was compared with that of the antibody-microstructures (right). In the bottom images, the ability of the MBL-microstructures (left) to detach the microorganisms was compared with that of the antibody-microstructures (right).

Referring to FIG. 4, larger amounts of the two different kinds of bacteria (*Pseudomonas aeruginosa* ATCC 27853 and *Staphylococcus aureus* ATCC 29213) were attached to the MBL-microstructures than to the antibody-microstructures. The bottom images show that the attached bacteria were much more efficiently detached from the MBL-microstructures than from the conventional antibody-microstructures. The bacteria isolated from the MBL-microstructures can also be reused. Accordingly, it could be confirmed that the MBL-coated microstructures to which all groups of bacteria were attached showed much higher reaction efficiency than the microstructures to which bacteria were attached based on specific reactions with the antibodies. These results suggest that larger numbers of the pure bacteria can be isolated from the MBL-coated microstructures within a short time in subsequent antibiotic susceptibility testing, demonstrating that the method of the present disclosure is advantageous in terms of time, cost, and sensitivity over conventional pure isolation and culture methods.

FIGS. 5 to 8 show the number of cells recorded every hour after four kinds of bacteria attached to the MBL-coated microstructures and the antibody-coated microstructures were isolated from the microstructures, followed by culture. The bacteria were *Pseudomonas aeruginosa* ATCC 27853 (FIG. 5), *Staphylococcus aureus* ATCC 29213 (FIG. 6), *Escherichia coli* ATCC 25922 (FIG. 7), and *Enterococcus faecalis* ATCC 29212 (FIG. 8).

In each figure, (a) shows the numbers of the bacterial cells derived from the MBL-coated microstructures and (b) shows the numbers of the bacterial cells derived from the antibody-coated microstructures.

Referring to FIGS. 5 to 8, the bacteria isolated from the MBL-microstructures grew more rapidly than the bacteria isolated from the antibody-microstructures. The numbers in the figures indicate the number of the bacteria per ml. When the number of bacteria reached $10^7$ or more, as indicated by the red numbers, antibiotic susceptibility testing can be performed.

The results of FIGS. 5 to 8 reveal that the activities of the bacteria attached to and detached from the MBL-microstructures were higher than those of the bacteria attached to and detached from the antibody-microstructures.

Although the present disclosure has been described in detail with reference to the foregoing embodiments, those skilled in the art will appreciate that various variations and modifications can be made to the embodiments without departing from the spirit and scope of the present disclosure as disclosed in the appended claims.

The invention claimed is:

1. A structure for capture and release of microorganisms, comprising:
    a microstructure,
        wherein the microstructure includes a protective layer and the protective layer is a silica-coated layer; and
    a protein coated on the microstructure with the protein directly contacting the microstructure, wherein the protein is capable of attaching and detaching the microorganisms,
    wherein the protein is a calcium-dependent serum protein,
    wherein the microstructure supports the protein coated on the microstructure and the microorganisms attached and detached to the protein.

2. The structure according to claim 1, wherein the protective layer further comprises functional groups.

3. The structure according to claim 1, wherein the microstructure is based on a hydrogel and a curable material, wherein the curable material includes silicon-containing polymers selected from the group consisting of polydimethylsiloxane, polyacrylamide, polyethylene oxide, polyethylene glycol diacrylate, polypropylene glycol diacrylate, polyvinyl pyrrolidone, polyvinyl alcohol, polyacrylate, and copolymers thereof.

4. The structure according to claim 1, wherein at least one of the width, thickness, and length of the microstructure is from 1 µm to 1 mm.

5. The structure according to claim 1, wherein the microstructure is a planar or disc-shaped structure.

6. The structure according to claim 1, wherein the microstructure further comprises a magnetic material.

7. The structure according to claim 1, wherein the protein is capable of attaching and detaching the microorganisms by artificial control, and wherein the artificial control varies at least one factor selected from the group consisting of pH, temperature, and external metal ion concentration.

8. The structure according to claim 1, wherein the calcium-dependent serum protein is a mannose-binding lectin (MBL).

9. A method for capture and release of microorganisms using microstructures, comprising:

providing microstructures;

wherein the microstructures include a protective layer and the protective layer is a silica-coated layer;

directly contacting a protein to the microstructures, wherein the protein is capable of attaching and detaching microorganisms, wherein the protein is a calcium-dependent serum protein, wherein the microstructures support the protein coated on the microstructures and the microorganisms attached and detached to the protein;

mixing the microstructures with a solution containing substances assisting in attachment of microorganisms in a solution containing microorganisms to prepare a mixed solution;

stirring the mixed solution to attach the microorganisms to the microstructures;

separating the microorganism-attached microstructures from the mixed solution; and exposing the microorganism-attached microstructures to an environment where the substances assisting in attachment of the microorganisms are present at a low concentration such that the microorganisms are detached from the microstructures due to the low concentration of the substances, and wherein the substances assisting in the attachment and detachment of the microorganisms are calcium ions.

10. The method according to claim 9, wherein the protein is a mannose-binding lectin (MBL).

11. The method according to claim 9, wherein the microorganisms are attached to the microstructures in the presence of the calcium ions at a concentration of 20 mM or higher.

12. The method according to claim 9, wherein the microorganisms are detached from the microstructures in the presence of the calcium ions at a concentration of 1 mM or less.

13. A method for capture and release of microorganisms using microstructures, comprising:

providing microstructures, wherein the microstructures include a protective layer and the protective layers is a silica-coated layer;

directly contacting a protein to the microstructures, wherein the protein is capable of attaching and detaching microorganisms, wherein the protein is a calcium-dependent serum protein, wherein the microstructures support the protein coated on the microstructures and the microorganisms attached and detached to the protein;

mixing the microstructures with a solution containing substances assisting in attachment of microorganisms in a solution containing microorganisms to prepare a mixed solution;

stirring the mixed solution to attach the microorganisms to the microstructures;

separating the microorganism-attached microstructures from the mixed solution; and exposing the microorganism-attached microstructures to an environment free of the substances used in assisting the attachment of the microorganisms such that the microorganisms are detached from the microstructures, and wherein the substances assisting in the attachment and detachment of the microorganisms are calcium ions.

* * * * *